(12) United States Patent
Ueda et al.

(10) Patent No.: US 6,601,970 B2
(45) Date of Patent: Aug. 5, 2003

(54) LINEAR LIGHTING SYSTEM

(75) Inventors: Hiroshi Ueda, Uji (JP); Kunio Kuroda, Uji (JP); Yuzo Nakayama, Uji (JP)

(73) Assignee: Kyoto Denkiki Co., Ltd., Uji (JP)

( * ) Notice: Subject to any disclaimer, the term of this patent is extended or adjusted under 35 U.S.C. 154(b) by 52 days.

(21) Appl. No.: 09/895,177

(22) Filed: Jul. 2, 2001

(65) Prior Publication Data

US 2002/0006039 A1 Jan. 17, 2002

(30) Foreign Application Priority Data

Jul. 14, 2000 (JP) ........................................ 2000-249023
Mar. 7, 2001 (JP) ........................................ 2001-063378

(51) Int. Cl.[7] ................................................. F21S 4/00
(52) U.S. Cl. ........................ 362/217; 362/216; 362/227; 362/249; 362/241; 362/247; 362/296; 362/16; 362/11; 362/260
(58) Field of Search ................................. 362/217, 216, 362/227–249, 241, 247, 260, 255, 296, 347, 16, 11

(56) References Cited

U.S. PATENT DOCUMENTS 1,763,630 A * 6/1930 Hopkins ........................ 355/63
4,891,739 A * 1/1990 Yasuda ........................ 362/296
5,822,053 A * 10/1998 Thrailkill ................. 356/237.1

* cited by examiner

Primary Examiner—Sandra O'Shea
Assistant Examiner—Bertrand Zeade
(74) Attorney, Agent, or Firm—Oliff & Berridge, PLC (57) ABSTRACT

The present invention relates to a linear lighting system with a linear light source. According to the invention, all the effective light around the optical axis emitted from the linear light source is introduced to a concave reflector so that the illumination is carried out only with the reflected light. The reflected light is controlled to be a converging or parallel beam of light so that a desired area is illuminated and the luminance is increased. In a mode of the invention, a cylindrical concave reflector 2 whose section taken vertical to a linear light source 1 is a part of an ellipse 2e having a first focus F1 at the linear light source 1 and a second focus F2 at an irradiation plane 3 (irradiation target point). The part of the ellipse covers an effective emission angle 2θ of the linear light source 1, and a reflected light produced at the part from a light within the effective emission angle 2θ is free of obstruction by the linear light source 1. In another mode, the cylindrical concave reflector 2 is a part of a parabola having a focus at the linear light source 1. The part of the parabola covers an effective emission angle 2θ of the linear light source 1, and a reflected light produced at the part from a light within the effective emission angle 2θ is free of obstruction by the linear light source 1.

14 Claims, 8 Drawing Sheets

1   LINEAR LIGHT SOURCE
1a  LED
2   REFLECTOR
2a  REFLECTIVE SURFACE
2e  ELLIPSE

Fig. 1

| | |
|---|---|
| 1 | LINEAR LIGHT SOURCE |
| 1a | LED |
| 2 | REFLECTOR |
| 2a | REFLECTIVE SURFACE |
| 2e | ELLIPSE |

LINEAR LIGHTING SYSTEM

The present invention relates to a lighting system used in such equipment as imaging devices for recognizing and/or examining an object using a camera, and particularly to a lighting system having a linear light source and a reflector suitable for the light source.

BACKGROUND OF THE INVENTION

In order to obtain an intended image using a camera, it is necessary to select an optimal lighting system suitable for that purpose. One practical example of such lighting systems is an LED lighting system including a linear light source having plural LEDs (light-emitting diodes) arranged in a row and a reflector (or reflectors) having a cylindrical reflective surface whose section is concave. The LED lighting system illuminates the longitudinal area of an object.

Figure 7:
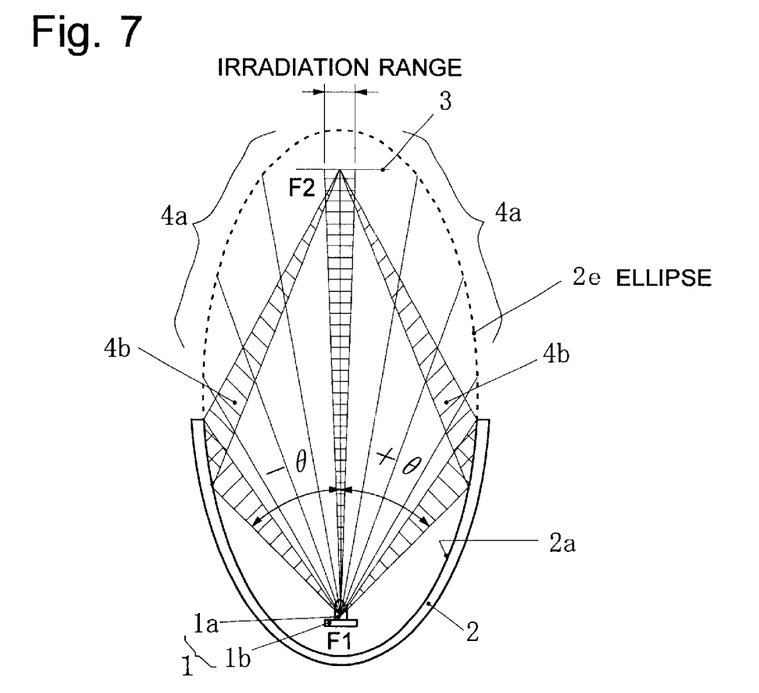
FIG. 7 is a section showing the structure of a conventional linear lighting system.

FIG. 7 is a section of a practically used LED lighting system, taken vertical to the longitudinal direction. In FIG. 7, numeral 1a denotes an LED packaged with resin or glass, and numeral 1b denotes a longitudinal board equipped with plural LEDs 1a. The LEDs 1a are arranged in a row on the board 1b at proper intervals. Thus, the LEDs 1a and the board 1b construct a linear light source 1. Numeral 2 denotes a reflector for reflecting a part of the light emitted from the linear light source 1. The optical axis of the linear light source 1 coincides with that of the reflector 2. Numeral 2a denotes a reflective surface of the reflector 2, whose section is concave. The reflective surface 2a is mirror-finished by a vapor deposition or plating of metal such as aluminum, or by plastering a tape or the like. The form of the concave section is generally an aspherical quadratic curve such as an ellipse or parabola. In the example of FIG. 7, the section is elliptical, and the linear light source 1 is disposed at or proximate to one (F1) of the two focuses of the ellipse. Numeral 3 denotes an irradiation plane disposed proximate to another focus F2 of the ellipse. Such an optical construction is based on the optical characteristic of an ellipse that all the light emitted from one focus is reflected by the elliptical surface and converges to another focus. The irradiation plane 3 is set to face the linear light source 1 and the reflector 2. When the concave section is designed parabolic and the light source is located at the focus of the parabola, the parabolic surface reflects the light and yields a parallel beam of light.

In the above LED lighting system, the light emitted from the linear light source 1 radially spreads like a solid angle around the optical axis. As the light spreads broader, the optical aberration of the LED 1a increases. Therefore, in general, the light within a preset solid angle around the optical axis is used as an effective light. In FIG. 7, the range of the effective light (effective emission angle) is shown as 2θ. Also, when an LED is designed for illuminating not a large area but a limited area of an object, the intensity of light emitted from the LED decreases as the spreading angle of light around the optical axis increases. Therefore, practically, the light utilized for illumination is mostly composed of a high intensity light within a narrow angle range around the optical axis, and a low intensity light surrounding the high intensity light is utilized merely supplementarily. As a result, the high intensity light directly illuminates the irradiation plane 3, and the surrounding low intensity light is first reflected by the reflector 2 and then illuminates the irradiation plane 3. In FIG. 7, the former is shown as a direct light 4a and the latter as a reflected light 4b.

Generally, the direct light 4a is a diverging light, so that the direct light 4a illuminates a broadened area on the irradiation plane 3. Thus, it is only the light within a limited angle around the optical axis that effectively illuminates a desired area, while most of the direct light 4a illuminates outside of the desired area, thus being wasted. Further, the light illuminating the outside area is reflected by walls around and turns into a scattered light (which is called "stray light"). The scattered light often badly influences the examination or the like, so that it must be eliminated by some means. Therefore, for example, a shielding plate having a narrow aperture is disposed close to the irradiation plane 3. In another example, the lens of the LED package is designed so that the emitted light converges only onto a desired area. The LED, however, lacks universal availability because it is designed for a particular distance between the linear light source 1 and the irradiation plane 3 and for a particular illumination area. When it is desired to locate the irradiation plane 3 as far from the linear light source 1 as possible, or when it is desired to reduce the illuminated area on the irradiation plane 3 as small as possible, the amount of wasted part of the direct light 4a increases. In this case, the amount of part of the direct light 4a reaching the irradiation plane 3 decreases, so that the luminance on the irradiation plane 3 decreases. Thus, in the illumination by the direct light 4a, some light wastage is inevitable.

The reflected light 4b, on the other hand, is a converging light, and all the light reflected by the reflective surface 2a converges to the irradiation plane 3. Therefore, in the illumination by the reflected light 4b, no light is wasted.

Thus, the conventional LED lighting system utilizes the direct light 4a that has a high intensity but is scattered and the reflected light 4b that is converged but has a low intensity, so that the efficiency is low.

The above problem might be solved by increasing the amount of the reflected light 4b while minimizing the amount of the wasted part of the direct light 4a. In order to attain that objective, however, it is necessary to greatly increase an effective diameter of the reflective surface 2a. Such a design is impractical because the reflector 2 would be so large that it would extend toward the irradiation plane.

Figure 8:
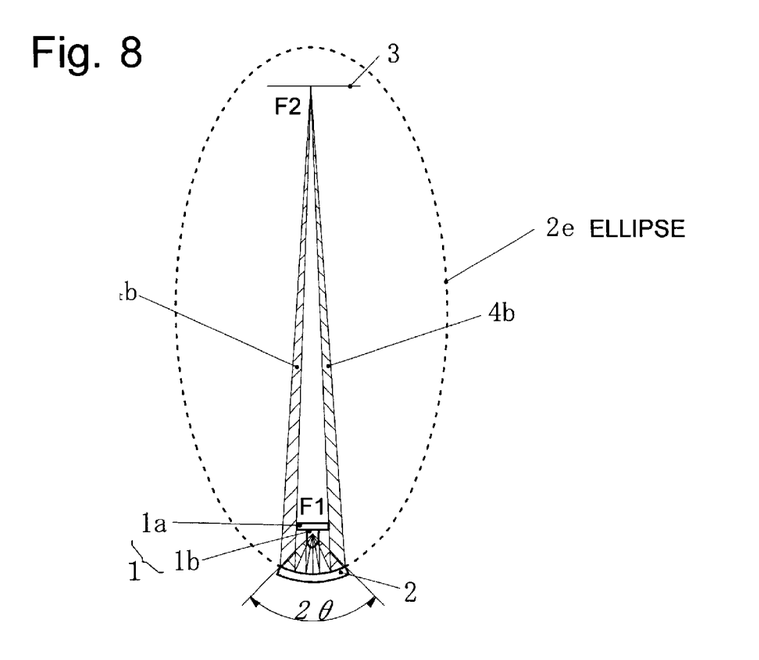
FIG. 8 is a section showing a conventional method of reflecting light.

One possible improvement to the prior art is to locate the linear light source 1 to face the reflector 2 so that the light emitted from the linear light source 1 around the optical axis is introduced to the reflector 2. FIG. 8 shows a section of an LED lighting system, taken vertical to the longitudinal direction, where the optical axis of the linear light source 1 coincides with that of the reflector 2 and the linear light source 1 is set to face the reflector 2. In this system, all the light spreading within a narrow angle around the optical axis and having a high intensity (i.e. the light propagating within the effective emission angle) is introduced to the reflector 2. However, part of the light within the effective emission angle, particularly the central part of the light including the optical axis and having a very high intensity, is obstructed by the linear light source 1 and/or the board 1b after being reflected by the reflector 2. As a result, that part of the light cannot reach the irradiation plane 3 and is wasted. In FIG. 8, the part around the optical axis where no hatching is done corresponds to the wasted part of the light. Thus, contrary to the expectation, the luminance on the irradiation plane 3 decreases, which prevents a practical use of the system.

Figure 9:
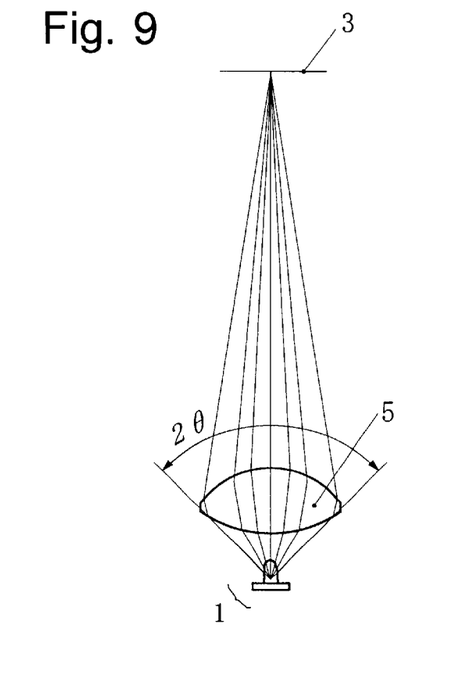
FIG. 9 is a section showing the structure of a conventional lighting system using a lens.

A method of efficiently using the direct light 4a is known where a cylindrical lens is employed instead of the reflector. FIG. 9 shows a section of a lighting system using a cylindrical lens, taken vertical to the longitudinal direction.

Numeral 5 denotes the cylindrical lens, which is formed to have an aspherical section so that it receives an effective light from the linear light source 1 within the angle 2θ around the central axis and effectively converges the light to the irradiation plane 3. The production cost of the lens 5, however, is very high whether it is manufactured by a grinding of glass materials or by a molding of resin. In practice, the lens is required to be inexpensive to form. Therefore, only such lenses having a simple form and structure are practically available. Examples of such lenses are: a lens having a hemispherical section; a lens shaped like a rod; a cylindrical lens of a small diameter in section, etc.

Regarding other types of light sources constructed without LEDs, a cathode-ray tube is one of the most commonly known linear light sources. A typical example is a cold cathode-ray tube used in a backlight of a liquid crystal display. The cold cathode-ray tube employs a reflector to utilize as much light as possible. In general, a cathode-ray tube has a circular section taken vertical to the longitudinal direction of the tube, and the surface of the tube is processed to diffuse a light. By such a construction, light is irradiated from the whole surface of the tube in all directions with an equal intensity. There, the amount of light irradiated in the direction opposite to the irradiation plane 3 cannot be ignored. Therefore, it is necessary to introduce the light to the irradiation plane with the reflector. Thus, the reflector is indispensable.

Thus, the effect of the reflector differs depending on whether the light source is a cathode-ray tube or LEDs because of the difference in the state of light and the purpose of illumination. When the cathode-ray tube is used, the reflected light and the direct light are equally utilized. When, on the other hand, LEDs are used, the high intensity light within a narrow effective emission angle around the optical axis is mainly utilized as the direct light, whereas the surrounding low intensity light is less expected to be utilized. Thus, the conventional LED lighting system inefficiently wastes a considerable amount of light other than the light near the optical axis.

As described above, according to the prior art, a LED lighting system including a linear light source having LEDs arranged in a row and a reflector having a concave section and a cylindrical reflective surface is constructed so that the light emitted from the linear light source is separated into a direct light and a reflected light. The direct light is a diverged light, so that the illumination by the direct light covers a larger area than the desired area. Therefore, a considerable amount of the direct light having a high intensity is inevitably wasted, and the luminance on the irradiation plane cannot be increased. The luminance might be increased by using a lens, which, however, is very costly.

Besides, when only a desired area is to be illuminated, it is necessary to employ a shield, which consumes time and labor.

SUMMARY OF THE INVENTION

The present invention is designed to address the above problems. With this invention, all the effective light around the optical axis emitted from the linear light source is introduced to the reflector so that the illumination is carried out only with the reflected light. The reflected light is controlled to be a converging or parallel beam of light so that a desired area is illuminated and the luminance is increased.

Thus, in the first aspect of the present invention, a linear lighting system is proposed with a linear light source and a concave reflector having a cylindrical concave surface, which is characterized by the fact that a section of the concave surface, taken vertical to the linear light source, is part of an ellipse having a first focus at the linear light source and a second focus at an irradiation target point, where the part of the ellipse covers an effective emission angle of the linear light source and a reflected light produced at the part from the light within the effective emission angle is free of obstruction by the linear light source.

In a second aspect of the present invention, a linear lighting system is proposed with a linear light source and a concave reflector having a cylindrical concave surface, which is characterized by the fact that a section of the concave surface, taken vertical to the linear light source, is a part of a parabola having a focus at the linear light source, where the part of the parabola covers an effective emission angle of the linear light source and a reflected light produced at the part from the light within the effective emission angle is free of obstruction by the linear light source.

The "cylindrical concave surface" is not restricted to the inside of a cylinder having geometrically circular section, but it includes any concave surface formed by a linear movement of an ellipse or parabola in a direction vertical to a plane on which the ellipse or parabola lies.

The light source and the irradiation target point need not exactly be at the focus. Even when they are slightly displaced from the focus, the object of the present invention can be attained. Accordingly, the term "focus" includes not only the geometrical focus but also an area proximate to the geometrical focus. Further, the linear light source need not be straight. For example, it may be slightly curved around a point located on the side of the irradiation target point (or target line) farther or closer than the target point or line.

BRIEF DESCRIPTION OF THE DRAWINGS

Preferred modes and an embodiment of the invention will be described below, referring to the attached drawings wherein.

DETAILED DESCRIPTION OF PREFERRED MODES AND EMBODIMENT

[First Mode of the Invention]

Figure 1:
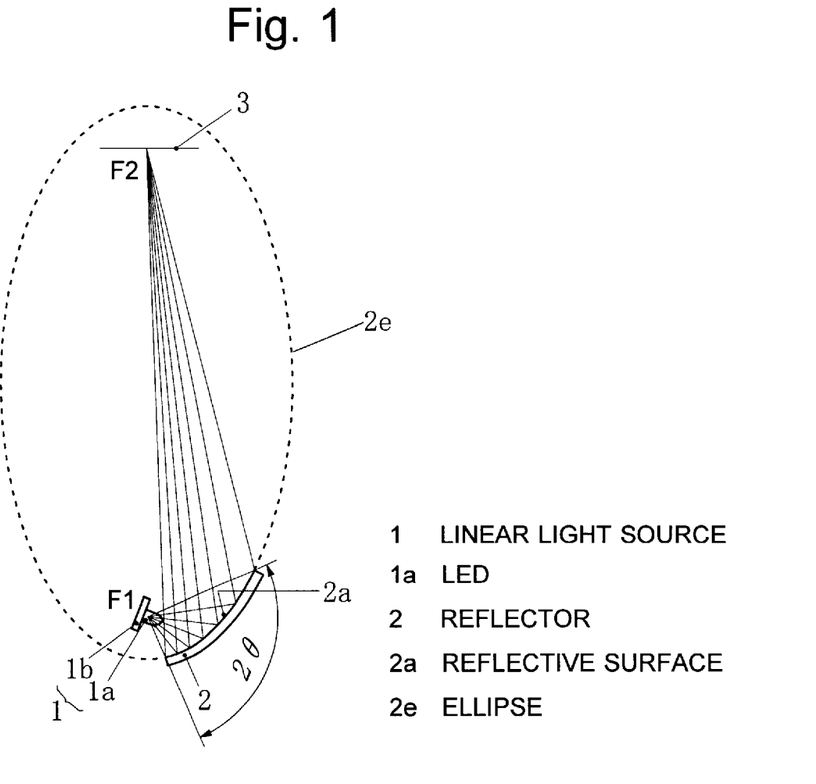
FIG. 1 is a section showing the structure of a first mode of the linear lighting system according to the present invention.

FIG. 1 is a schematic diagram of a first mode of a linear lighting system according to the present invention, showing the arrangement of optical elements at a section taken vertical to the longitudinal direction of the linear light source. In FIG. 1, those elements already shown in FIG. 7 are denoted by the same numerals and will not be described in detail below. In FIG. 1, the reflective surface 2a of the reflector 2 has a concave section and corresponds to a part of an ellipse 2e (aspherical quadratic curve). The linear light source 1 is located at one of the two focuses of the ellipse 2e (first focus F1), and the irradiation plane 3 is located at another focus (second focus F2). A slight displacement of the linear light source and/or the irradiation plane 3 from the focus may be practically allowed. In some cases, it is recommendable to make an intentional displacement from the focus to appropriately broaden the irradiation area if necessary. By the above construction, the light emitted from the linear light source 1 within the effective emission angle around the optical axis is reflected by the reflective surface 2a of the reflector 2 and converges to the irradiation plane 3. It should be understood that each of the first focus F1 and the second focus F2 of the cylindrical reflective surface extends like a straight or curved line in the three-dimensional space.

Most of the light emitted from the linear light source 1 is irradiated within the effective emission angle around the optical axis (the range 2θ in FIG. 1). In the present mode of the invention, the optical axis of the linear light source 1 is inclined from the line passing the two focuses F1–F2 (longitudinal axis). The reflector 2 is posed so that the reflective surface 2a covers the effective emission angle (2θ) of the linear light source 1 arranged as described above. Thus, in the present mode of the invention, the linear light source 1 faces neither the reflective surface 2a of the reflector 2 nor the irradiation plane 3. By such an arrangement, all the light emitted from the linear light source 1 within the effective emission angle is reflected by the reflector 2 and converges to the irradiation plane 3 without being obstructed by the LED 1a and/or the board 1b.

Figure 2:
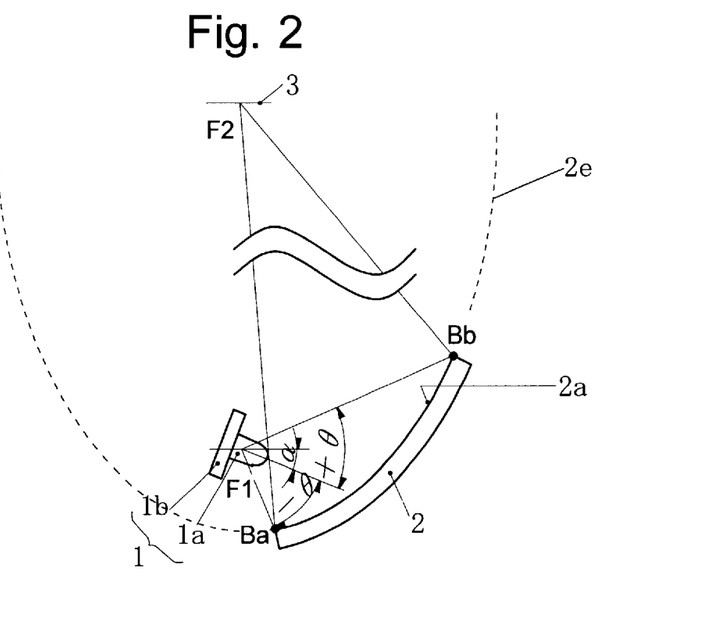
FIG. 2 is an enlarged section of a part of the first mode of the present invention.

For example, the arrangement of the elements is determined as follows. FIG. 2 is an enlarged section of the linear light source 1 and the reflector 2. In FIG. 2, the angle by which the optical axis of the linear light source 1 is inclined from the minor axis of the ellipse 2e is denoted by a. The first step is to define the ellipse 2e. There are innumerable ellipses having the focuses at F1 and F2, and one ellipse is selected taking account of the size of the mirror system and/or the position of the irradiation plane. The next step is to determine the inclination angle a of the linear light source 1 and the position of the reflective surface 2a of the reflector 2 as follows. First, the inclination angle a and one border Ba of the reflective surface 2a are determined so that an outermost beam of light emitted from the linear light source 1 and travelling along a path at the angle −θ from the optical axis is not obstructed by the linear light source 1 itself (LED 1a and board 1b) after being reflected by the ellipse 2e. Also, the point where another outermost beam of light (optical axis +θ) within the effective emission angle is reflected by the ellipse 2e is determined as the other border Bb of the reflective surface 2a.

Figure 3:
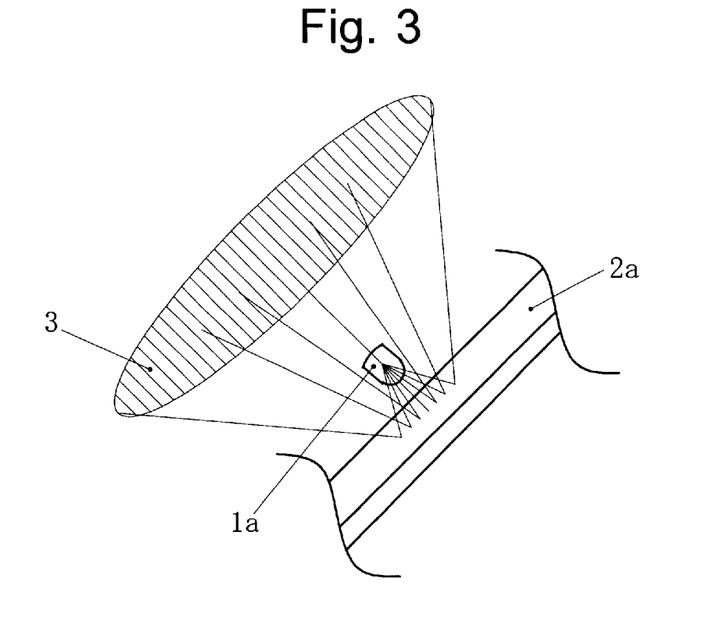
FIG. 3 is a perspective view showing a reflection of light by a cylindrical reflector.

FIG. 3 is a perspective view showing a reflection of light by a cylindrical reflective surface 2a. In FIG. 3, for the convenience of explanation, the cylindrical reflective surface 2a is shown as a longitudinal section, and the illumination is performed only with a single LED. The reflection of light in a plane vertical to the longitudinal direction of the cylindrical reflective surface 2a occurs as described above. The reflection of light in the longitudinal direction occurs in the same manner as a reflection by a flat surface. That is, in the longitudinal direction of the linear light source 1, the reflected light does not converge but spreads. Therefore, when a single LED is used, the reflected light illuminates an elongated elliptical area on the focal line of the second focus F2 of the cylindrical reflective surface 2a, as shown in FIG. 3.

Figure 4:
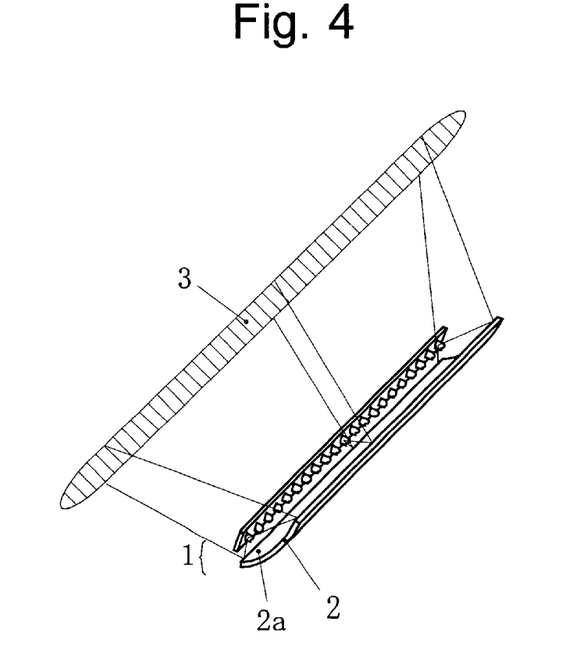
FIG. 4 is a perspective view showing the state of illumination by the first mode of the invention.

When, however, multiple LEDs are arranged in a row to construct a linear light source, the lights of the LEDs overlap on the focal line of the second focus F2 and form a longitudinal narrow illumination area having a constant width, as shown in FIG. 4. As the spatial interval of the LEDs is decreased, the illumination areas overlap more densely, whereby the irradiation plane 3 is illuminated evenly with an increased luminance.

Thus, by the first mode of the invention, the optical axis of the LED 1a is inclined by a preset angle so that all the light emitted from the linear light source 1 within the effective emission angle around the optical axis is introduced to the reflector 2. Thus, the illumination is performed only with the reflected light. The reflective surface 2a is formed to have a quadratic aspherical section. When the section is elliptical, the LED 1a is located at or proximate to the first focus of the ellipse, and the irradiation plane 3 is located at or proximate to the second focus. By such a construction, all the reflected light converges to the irradiation plane 3 and illuminates the plane 3 with a high and even luminance.

Though not shown in the drawing, the ellipse may be replaced with a parabola. In this case, the linear light source 1 is located at or proximate to the focus of the parabola so that all the light within the effective emission angle is introduced to the reflective surface. The light reflected within a plane vertical to the longitudinal direction of the cylindrical reflective surface becomes a parallel beam of light. In the longitudinal direction, the cylindrical reflective surface reflects light like a flat surface, as in the case of FIG. 3, so that the light spreads as it propagates after the reflection. As a result, the irradiation plane 3 is illuminated at a longitudinal narrow area, as in the case of ellipse. What is different from the case of ellipse is that the width of the illuminated area is constant irrespective of the distance of the irradiation plane and that the luminance does not change depending on the distance of the irradiation plane. Thus, in the case of parabola, the reflected light becomes a parallel beam of light and illuminates a longitudinal narrow area having a constant width. Thus, all the reflected light is utilized for the illumination.

The reflector 2 of the first mode of the invention is manufactured as follows. The most important part of the reflector 2 is the reflective surface 2a, which can be conveniently formed by a press. For example, the reflector 2 is obtained by cutting a mirror-finished material, such as a thin metal plate with a metal foil plastered on one side, into a desired size and pressing it into a desired form. This is a well-known method of forming a reflector of a cold cathode-ray tube used as a light source of a backlight of a liquid crystal display. Different from an injection molding of a lens, the above method requires less initial cost for mass production because it requires only a simple system for pressing thin metal plate.

[Second Mode of the Invention]

Figure 5:
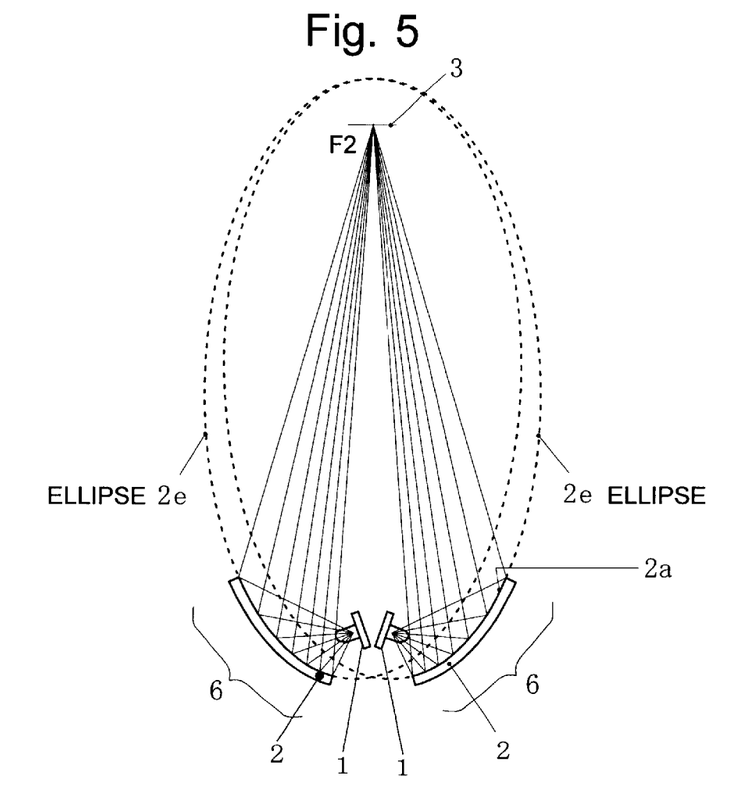
FIG. 5 is a section showing the structure of a second mode of the present invention.

A second mode of the invention is described referring to FIG. 5. FIG. 5 shows the arrangement of optical elements at a section taken vertical to the longitudinal direction of the linear light source 1, similar to FIG. 1. In the present mode of the invention, two linear lighting systems 6, 6 are used, where each system 6 is constructed as shown in FIG. 1 including a linear light source 1 having plural LEDs arranged in a row and a reflector 2 having a cylindrical reflective surface 2a whose section is concave. The linear lighting systems 6, 6 are arranged so that the linear light sources 1, 1 are posed back to back and that the second focuses F2 of the ellipses 2e, 2e almost overlap on the irradiation plane 3. By such a construction, the light emitted from the two linear light sources 1, 1 are reflected by the reflectors 2, 2 and converge to the same irradiation plane 3. As a result, the amount of light converging on the irradiation plane 3 is doubled and, accordingly, the luminance is doubled. Thus simply arranging the same linear lighting systems 6, 6 back to back, the luminance is doubled without consuming time and labor. Each of the reflectors 2, 2 utilizes only a half of the ellipse 2e across the optical axis. Accordingly, even when the two linear lighting systems 6, 6 are coupled together, the total size of the reflectors 2, 2 is almost the same as used in the conventional system shown in FIG. 7. Further, in the second mode of the invention, it is not difficult to construct the reflectors 2, 2 as an integral body since they are posed so that the concave surfaces having the same section face each other.

In the system of FIG. 5, the sections of the reflectors 2, 2 are assumed as parts of the ellipses 2e, 2e. The sections may be otherwise parts of parabolas. In this case, each of the reflectors 2, 2 yields a parallel beam of light. By posing the reflectors 2, 2 so that the parallel beams cross at the irradiation plane 3, the luminance on the irradiation plane 3 can be doubled, as described above.

The two linear lighting systems 6, 6 may be constructed so that their positions around the irradiation plane 3 can be changed. By changing their positions, an object placed on the irradiation plane 3 can be illuminated with arbitrary irradiation angles. For example, when a shaded image of an object is desired, or when an object having a solid structure is to be illuminated from the side, desired results can be obtained by positioning the linear lighting systems 6, 6 at appropriate irradiation angles.

Thus, the lighting system of the second mode of the invention can be constructed by simply coupling the two linear lighting systems 6, 6 back to back. The luminance is easily increased without making the system bulky. Further, by constructing the linear lighting systems 6, 6 so that the irradiation angles are variable, an object can be illuminated from various angles.

[Third Mode of the Invention]

Figure 6:
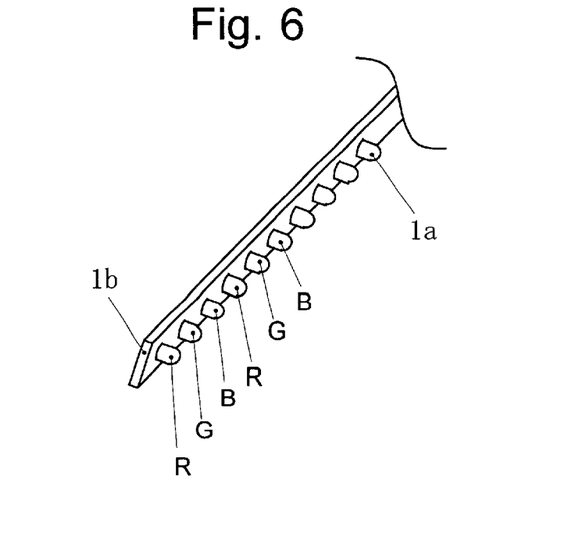
FIG. 6 is a perspective view of the structure of a third mode of the present invention.

A third mode of the invention is described referring to FIG. 6. FIG. 6 is a perspective view showing the structure of a linear light source 1 used in the present mode of the invention. In the present mode, the linear light source 1 includes plural types of LEDs 1a having different emission wavelengths (luminescent colors) arranged in order on the board 1b. Elements other than the linear light source 1 are the same as in the first and second modes of the invention. FIG. 6 shows, for example, that the LEDs 1a corresponding to the three primary colors of red (R), green (G) and blue (B) are arranged in order at equal intervals on the board 1b. The three colors of lights illuminate a longitudinal narrow area on the irradiation plane 3, overlapping each other. By selectively supplying power to the LEDs 1a, various illumination colors composed of a mixture of the three colors appear on the irradiation plane 3. For example, supply of power to all the R, G and B LEDs yields a white light. Further, by controlling the output of each LED 1a, a wider variety of illumination colors can be obtained.

In the reflection of light by a reflector, no color shift occurs on the irradiation plane because, in general, the incident angle and the reflecting angle do not depend on the wavelength. Thus, different from conventional systems using a lens to refract the light, the present mode of the invention is featured by the fact that the illumination is performed without a color shift.

Thus, by the third mode of the invention, various illumination colors can be obtained by selectively supplying power to the LEDs 1a of different emission wavelengths arranged in order, and by controlling outputs of the LEDs.

Figure 10A:
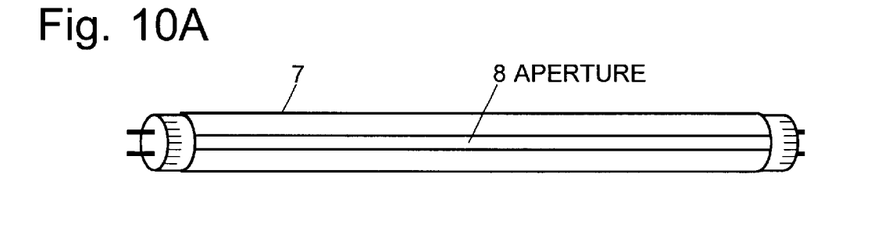
FIG. 10A is an outside view of an aperture fluorescent tube as an example of linear light sources.
Figure 10B:
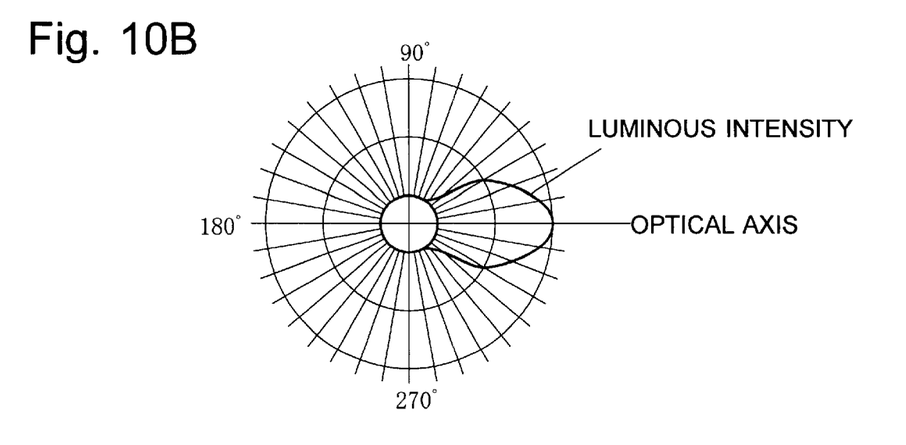
FIG. 10B is a graph showing the luminous intensity distribution of the tube.

In the above modes of the invention, an LED array is used as the light source. It is possible to use other types of light sources as the linear light source of the present invention. An example is an aperture fluorescent lamp 7 as shown in FIG. 10A. This device is manufactured by forming a reflecting film layer between the glass tube and the fluorescent substance of the fluorescent lamp 7 and by scratching a part of it to form a linear opening (aperture) 8. FIG. 10B shows the luminous intensity distribution of the lamp 7. The lamp 7 has the characteristic that it emits light with high intensities within a certain angle (effective emission angle) around the optical axis while it emits light with very low intensities outside the effective emission angle. The light emitted outside the effective emission angle is reflected by the reflecting film of the inner wall of the tube and is finally emitted from the aperture 8. Thus, most of the light is effectively utilized. By employing the lamp 7 as the light source of the linear lighting system of the present invention, the lighting efficiency is greatly increased owing to the combination of the high efficiency of the light source and the high efficiency of utilizing light by the present invention.

As described above, according to the present invention, the linear light source is posed to obliquely face the reflector. The light emitted from the linear light source within the effective emission angle around the optical axis is introduced to the reflector, and the reflected light travels without being obstructed. Thus, the light within the effective emission angle is fully reflected and utilized for illumination.

Further, when the section of the reflective surface is elliptical, all the reflected light converges to the irradiation plane located at or proximate to the second focal line, whereby the luminance on the irradiation plane increases. When the section of the reflector is parabolic, an illumination area of a constant width is obtained irrespective of the distance of the irradiation plane.

Further, the luminance can be easily doubled by arranging two linear light sources back to back. When the section of the reflective surface is elliptical, the two linear light sources are arranged so that their second focal lines coincide or substantially coincide with each other. When, on the other hand, the section of the reflective surface is parabolic, the two linear light sources are arranged so that the reflected parallel beams of light cross at the irradiation target point (or plane). Further, when the two linear light sources are constructed so that the irradiation angles can be varied, it is possible, for example, to decrease the shaded part of the object or to give an arbitrary shade to the object.

Further, when the linear light source is constructed using plural LEDs having different emission wavelengths (different luminescent colors), various illumination colors can be easily obtained by selectively turning the LEDs on and off and/or by controlling the outputs of the LEDs.

[Embodiment]

Figure 11:
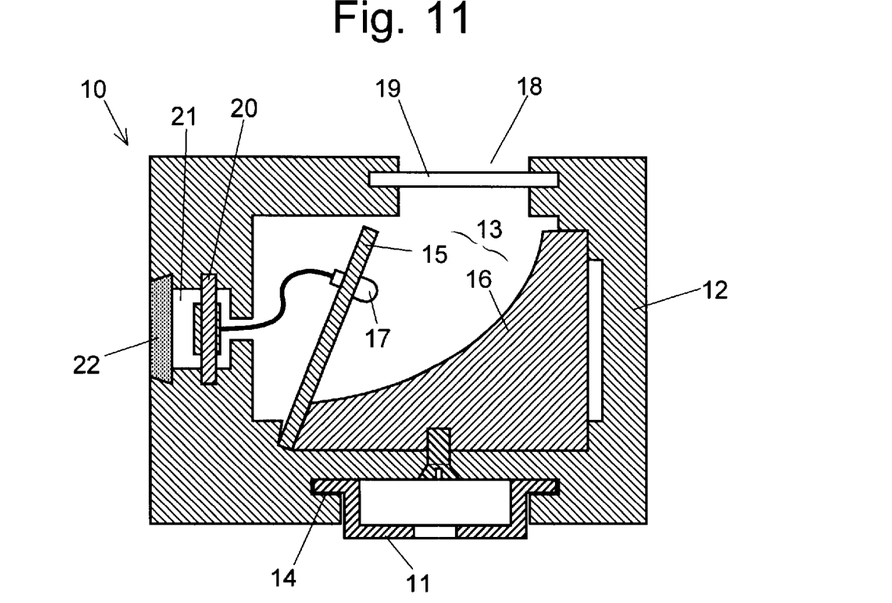
FIG. 11 is a section of a connection-type linear lighting system as an embodiment of the present invention.

As an embodiment of the linear lighting system according to the present invention, a connection-type linear lighting system is described referring to FIGS. 11–14. The linear lighting system of the present embodiment includes plural linear lighting system units having a preset length, which are arranged on a rail to be connected together to construct a linear lighting system having a desired length. FIG. 11 is a section of a linear lighting system unit 10 placed on a rail 11. The unit 10 includes a casing 12 with a lighting unit 13 fixed inside. The casing 12 is provided with a sliding groove 14 having a section corresponding to the section of the rail 11. Thus, the unit 10 can slide on the rail 11. The casing 12 is manufactured by extrusion of aluminum or plastic, for example.

Figure 12:
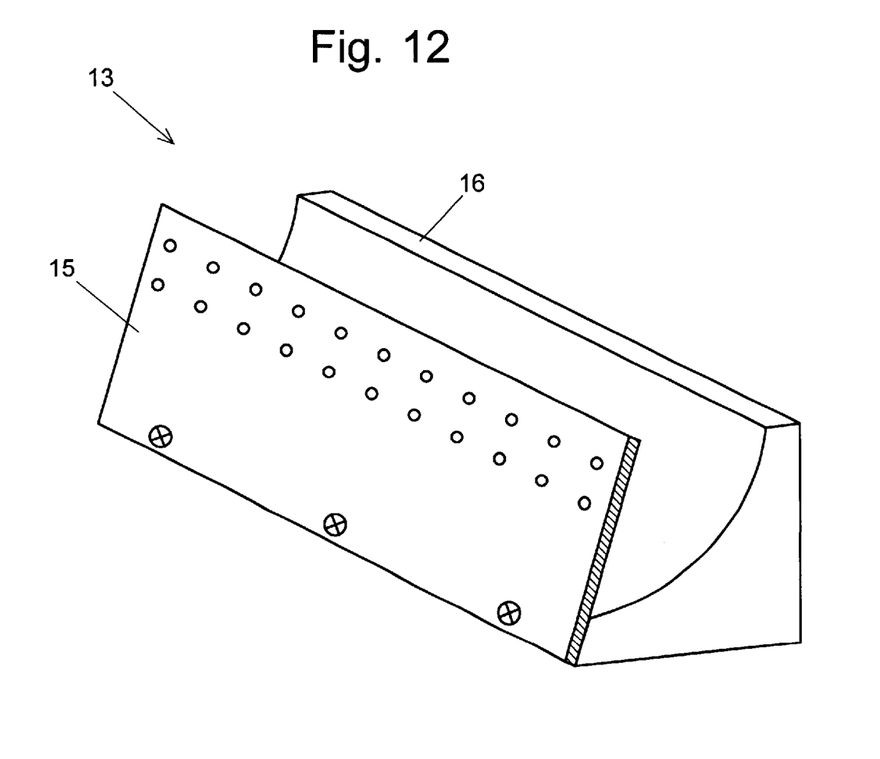
FIG. 12 is a perspective view of a lighting unit contained in the connection-type linear lighting system of the embodiment.

As shown in FIG. 12, the lighting unit 13 includes an LED holding board 15 and a reflector 16. The LED holding board 15 is fixed to the foot of the reflector 16 by threads, adhesive or the like. The LED holding board 15 consists of a printed board, where holes for connecting LEDs 17 are formed at preset intervals and a wiring is printed to connect the holes. The lead wires of the LED 17 are inserted into the holes and soldered to the printed wiring. The reflective surface of the reflector 16 is either elliptical or parabolic. The LED holding board 15 is fixed to the reflector 16 so that the light-emitting part of the LED 17 and the reflective surface come to the optical arrangement according to the preset invention. In order to reduce the cost, it is preferable to form the reflector 16 using resin, and to form the reflective surface by vapor deposition of metals such as aluminum.

In the upper part of the casing 12, a longitudinally extending opening 18 is provided, in which a transparent plate 19 made of acrylic resin or the like is fitted. The light emitted from the LED 17 and reflected by the reflective surface 16 passes through the opening 18 and is irradiated from the upper part to the outside. When the reflective surface of the reflector 16 is elliptical, the light irradiated to the outside converges to a line at a certain distance from the upper part of the linear lighting system. When the reflective surface is parabolic, the light is irradiated from the opening 18 upwards as a parallel beam of light.

On the outside of one of the sidewalls of the casing 12 is formed a groove 21 for setting a power supply board 20. Holes are formed at the bottom of the groove 21 (or in the wall at the side of the lighting unit 13), each hole corresponding to each LED, and wires leading to the LEDs are passed through the holes. A guard plate 22 is fixed to the outside of the groove 21.

Figure 13:
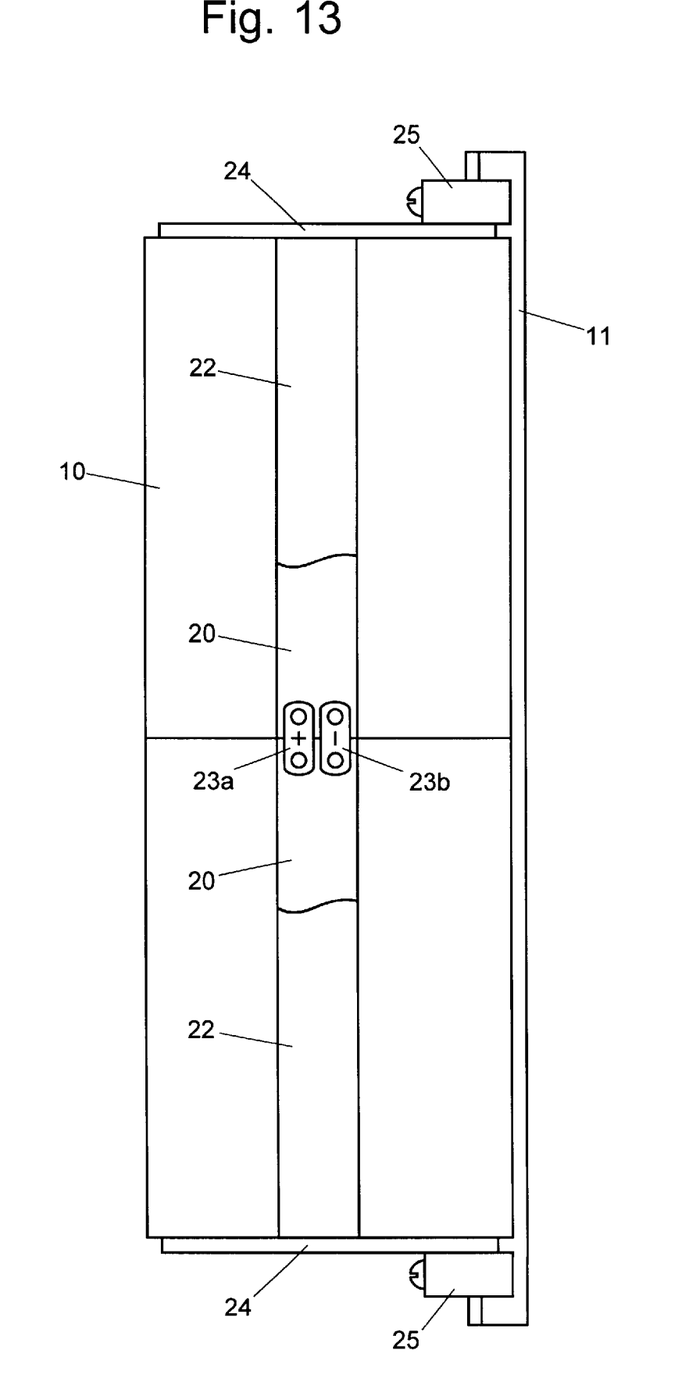
FIG. 13 is a side view showing a connected state of the connection-type linear lighting system of the embodiment.

As shown in FIG. 13, plural linear lighting system units 10 are arranged in a row on the rail 11, and both ends of the row are held via side plates 24 by fixing parts 25. The fixing parts 25 are fixed to the rail 11 by threads or the like. Two adjoining linear lighting system units 10 are electrically connected by a pair of fasteners 23a, 23b, positive and negative, which connect the power supply boards 20 of the two units 10. When a feeder line is connected to one unit linear lighting 10 located at the end, the power is supplied to all the LEDs 17 of all the units 10.

The linear lighting system unit 10 of the present embodiment can be used to construct a desired length of linear lighting system, as described above. It is of course possible to use one linear lighting system unit 10 separately without using the rail 11. The connection of the units 10 may be done either by users of the system when they use the system or by manufacturers before shipments of the system.

Figure 14:
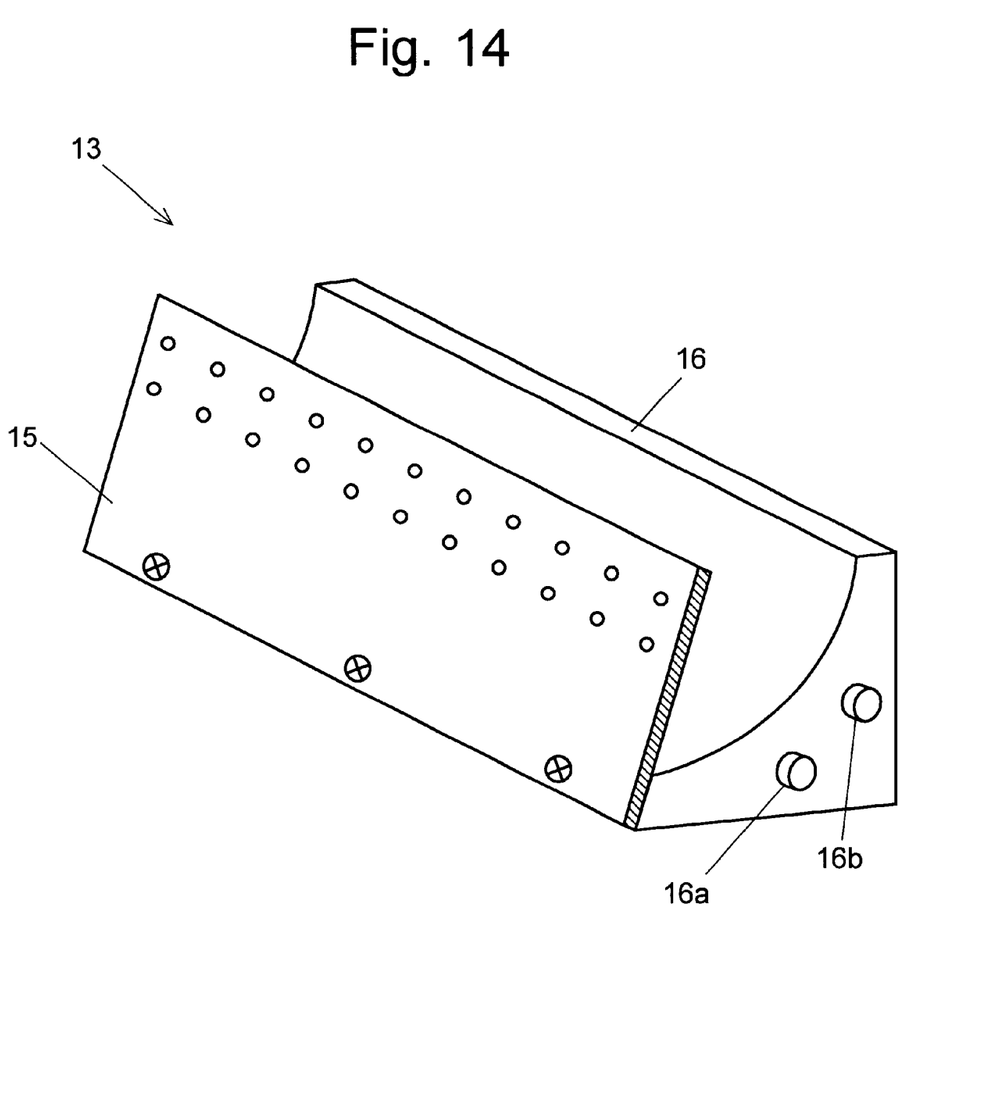
FIG. 14 is a perspective view showing another form of connecting the lighting units.

The connection of the linear lighting system units 10 may be done without using the rail 11. In FIG. 14, for example, the reflector 16 is provided with projections 16a, 16b at one end and holes (not shown) at the other end. Two reflectors 16 are connected together by engaging the projections 16a, 16b of one reflector 16 into the holes of the other reflector 16. By such a construction, plural lighting units 13 can be connected without using the casing 12.

What is claimed is:

1. A linear lighting system for converging light on a linear portion including a linear light source emitting light mostly in an effective emission angle and a concave reflector having a cylindrical concave surface, which is characterized in that a section of the concave surface, taken vertical to the linear light source, is part of an ellipse having a first focus at the linear light source and a second focus at a point of the linear portion, where the part of the ellipse covers the effective emission angle of the linear light source and a reflected light produced at the part from a light within the effective emission angle is free of obstruction by the linear light source.

2. A linear lighting system including a linear light source and a concave reflector having a cylindrical concave surface, which is characterized in that a section of the concave surface, taken vertical to the linear light source, is part of a parabola having a focus at the linear light source, where the part of the parabola covers an effective emission angle of the linear light source and a reflected light produced at the part from a light within the effective emission angle is free of obstruction by the linear light source.

3. The linear lighting system according to claim 1, comprising a plurality of the linear light sources and the concave reflectors corresponding to the linear light sources, wherein the concave reflectors share the target point as the second focuses thereof and each corresponding pair of the linear light source and the concave reflector are arranged as aforementioned in claim 1.

4. The linear lighting system according to claim 2, comprising a plurality of the linear light sources and the concave reflectors corresponding to the linear light sources, wherein the linear light sources and the concave reflectors are arranged so that all reflected lights produced by the concave reflectors cross at the irradiation target point.

5. The linear lighting system according to claim 3, wherein the linear light sources are constructed so that irradiation angles of the reflected lights are variable.

6. The linear lighting system according to claim 4, wherein the linear light sources are constructed so that irradiation angles of the reflected lights are variable.

7. The linear lighting system according to claim 1, wherein the linear light source is constructed using a plurality of light-emitting diodes arranged in a row.

8. The linear lighting system according to claim 2, wherein the linear light source is constructed using a plurality of light-emitting diodes arranged in a row.

9. The linear lighting system according to claim 7, wherein plural types of light-emitting diodes having different emission wavelengths are arranged.

10. The linear lighting system according to claim 8, wherein plural types of light-emitting diodes having different emission wavelengths are arranged.

11. The linear lighting system according to claim 1, wherein the linear light source is constructed using an aperture fluorescent lamp.

12. The linear lighting system according to claim 2, wherein the linear light source is constructed using an aperture fluorescent lamp.

13. A connection-type linear lighting system comprising a plurality of linear lighting system units to be placed on a rail and connected with each other, each linear lighting system unit including a casing with a lighting unit fixed inside, each lighting unit including the linear light source and the concave reflector as aforementioned in claim 1.

14. A connection-type linear lighting system comprising a plurality of linear lighting system units to be placed on a rail and connected with each other, each linear lighting system unit including a casing with a lighting unit fixed inside, each lighting unit including the linear light source and the concave reflector as aforementioned in claim 2.

* * * * *